(12) United States Patent
Barry et al.

(10) Patent No.: US 11,957,400 B2
(45) Date of Patent: Apr. 16, 2024

(54) RESECTOSCOPE SYSTEMS AND METHODS

(71) Applicant: American Endoscopic Innovations, LLC, Charlton, MA (US)

(72) Inventors: James Barry, Charlton, MA (US); Israel Franco, Chappaqua, NY (US); Michael Grasso, III, Rye, NY (US); Thomas Ruegg, Vancouver (CA)

(73) Assignee: American Endoscopic Innovations, LLC, Charlton, MA (US)

( * ) Notice: Subject to any disclaimer, the term of this patent is extended or adjusted under 35 U.S.C. 154(b) by 0 days.

(21) Appl. No.: 18/307,528

(22) Filed: Apr. 26, 2023

(65) Prior Publication Data
US 2023/0389978 A1    Dec. 7, 2023

Related U.S. Application Data

(63) Continuation of application No. 17/726,200, filed on Apr. 21, 2022, now Pat. No. 11,648,048.

(51) Int. Cl.
| | |
|---|---|
| *A61B 18/14* | (2006.01) |
| *A61B 1/00* | (2006.01) |
| *A61B 17/00* | (2006.01) |
| *A61B 18/00* | (2006.01) |

(52) U.S. Cl.
CPC .......... *A61B 18/14* (2013.01); *A61B 1/00087* (2013.01); *A61B 1/00096* (2013.01); *A61B 2017/0023* (2013.01); *A61B 2017/00424* (2013.01); *A61B 2018/00202* (2013.01); *A61B 2018/00517* (2013.01); *A61B 2018/00601* (2013.01); *A61B 2018/1475* (2013.01); *A61B 2217/007* (2013.01); *A61B 2218/002* (2013.01)

(58) Field of Classification Search
CPC ... A61B 18/14; A61B 18/1402; A61B 18/148; A61B 18/1482; A61B 2018/00601; A61B 2018/00035; A61B 2018/00011; A61B 2018/00029; A61B 2018/00607; A61B 2018/0097; A61B 2018/00982; A61B 2018/1407; A61B 2018/141; A61B 2018/1472; A61B 2018/1475; A61B 1/00096; A61B 2217/007; A61B 2218/002; A61B 2218/007
USPC ............ 606/41, 42, 45, 46; 607/98, 99, 101, 607/104, 105, 113, 115, 116
See application file for complete search history.

(56) References Cited

U.S. PATENT DOCUMENTS

| | | |
|---|---|---|
| 5,456,684 A | 10/1995 | Schmidt et al. |
| 5,902,272 A | 5/1999 | Eggers |
| 8,702,700 B2 | 4/2014 | Maeda et al. |

(Continued)

FOREIGN PATENT DOCUMENTS

| | | |
|---|---|---|
| JP | H0654801 A | 3/1994 |
| JP | 2008093019 A | 4/2008 |

(Continued)

*Primary Examiner* — Thomas A Giuliani
(74) *Attorney, Agent, or Firm* — Fish & Richardson P.C.

(57) ABSTRACT

A surgical device for examination and treatment of a target area. The surgical device includes a shaft portion that extends along a longitudinal axis and that is configured to be inserted into a patient's body, a surgical tool provided within the outer sheath and configured to be movable along the longitudinal axis, and an optical assembly provided at a distal end of the inner shaft, the optical assembly including a light source and an imaging sensor.

19 Claims, 11 Drawing Sheets

(56) References Cited

U.S. PATENT DOCUMENTS

| | | | |
|---|---|---|---|
| 9,474,438 B2 * | 10/2016 | Fan | A61B 1/00128 |
| 10,758,301 B2 | 9/2020 | Ciccone et al. | |
| 11,648,048 B1 * | 5/2023 | Barry | A61B 1/00096 |
| | | | 606/41 |
| 2015/0157387 A1 | 6/2015 | OuYang | |
| 2018/0125567 A1 * | 5/2018 | Ciccone | A61B 18/149 |

FOREIGN PATENT DOCUMENTS

| | | |
|---|---|---|
| JP | 2014018659 A | 2/2014 |
| WO | WO 2018089403 A1 | 5/2018 |

* cited by examiner

RESECTOSCOPE SYSTEMS AND METHODS

CROSS REFERENCE TO RELATED APPLICATION

This patent application is a continuation (and claims the benefit of priority under 35 USC 120) of U.S. patent application Ser. No. 17/726,200, filed Apr. 21, 2022, now U.S. Pat. No. 11,648,048. The disclosure of the prior application is considered part of (and is incorporated by reference in) the disclosure of this application.

TECHNICAL FIELD

This document describes devices, systems, and methods related to resectoscopes. Specifically, a device that can assist in treating patients while utilizing endoscopic or laparoscopic based therapies. For example, devices that can facilitate the examination of the anatomy of a patient using endoscopic or laparoscopic techniques, and facilitates the resection of tissues in a targeted location in the patient's body.

BACKGROUND

In general, minimally invasive medical procedures can utilize catheters, endoscopes, and other medical instruments to perform therapies and imaging to patients. Minimally invasive medical procedures can be complex and involve several medical instruments in use concurrently and/or at various times during a procedure.

Resectoscopes have been utilized for procedures to provide visual access to anatomy via a natural, laparoscopic, or percutaneous route. Therapeutic procedures can be performed utilizing attached instruments for cutting, ablating, and coagulating tissues. The instruments can be removable from the resectoscope so the instruments can be exchanged for a variety of purposes and for post-operative cleaning.

Previous approaches to reusable resectoscope systems have a larger outside diameter of the insertion shaft to accommodate the attachment of a high-frequency (HF) instrument and outer sheath. Previous approaches also utilize complex reprocessing of the resectoscope and other instruments to assure sterility, which can cause safety issues for the reusable instrument caused by sterile reprocessing of a narrow cannula. Previous resectoscope systems utilize expensive components including rod lens endoscopes that can include the addition of a camera system for viewing the anatomy on a video monitor. These expensive components are accompanied by ergonomic issues with the bulky resectoscope systems that are heavy, particularly when connected to the camera system. These systems can also include a complex assembly process performed by specialized personnel of multiple components, usually performed in the operating theater.

SUMMARY

The document generally relates to devices, systems, and methods related to resectoscopes. Specifically, a device that can assist in treating patients while utilizing endoscopic or laparoscopic based therapies.

One aspect includes a surgical device. The surgical device can have a shaft portion that extends along a longitudinal axis and that is configured to be inserted into a patient's body, the shaft portion may include: an outer sheath, an inner shaft provided within the outer sheath, a surgical tool provided within the outer sheath and configured to be movable along the longitudinal axis, and an optical assembly provided at a distal end of the inner shaft, the optical assembly including a light source and an imaging sensor. The device also includes a handle portion that is coupled to a proximal end of the shaft portion, the handle portion including a manipulator that is configured to be manipulated by a user to move the surgical tool along the longitudinal axis. A first channel that extends along the longitudinal axis is defined by one or both of the outer sheath and the inner shaft, the first channel providing a first flow path between the proximal end of the shaft portion and a first opening provided at a distal end of the shaft portion. A second channel that extends along the longitudinal axis is defined by one or both of the outer sheath and the inner shaft, the second channel providing a second flow path between the proximal end of the shaft portion and a second opening provided at the distal end of the shaft portion, the second flow path being distinct from the first flow path. The optical assembly is provided at a distal end of the first channel to thereby partially block and divert the first flow path around the optical assembly, and where the surgical tool is provided in the second channel and configured to be extended out of or retracted into the outer sheath via the second opening.

Implementations may include one or more of the following features. The optical assembly protrudes radially inward from an interior surface of the first channel. The first opening is defined between the optical assembly and the inner shaft to at least partially surround the optical assembly. The first opening is configured to direct fluid across a distal surface of the optical assembly. A cross-sectional area of the first channel is greater than a cross-sectional area of the first opening. The first channel is configured to impinge fluid against a proximal surface of the optical assembly. The first opening is configured to inject fluid to a surgical site, and the second opening is configured to suction or remove fluid and biologics from the surgical site. The handle portion includes: a first port that is in fluid connection with the first channel and that is configured to introduce fluid into the first channel, and a second port that is in fluid connection with the second channel and that is configured to extract fluid and biologics from the second channel.

In some implementations, the surgical tool is an electrode loop that is configured to be connected to a high-frequency power supply. The electrode loop is configured to operate in a monopolar mode based on being connected to a monopolar power supply and configured to operate in a bipolar mode based on being connected to a bipolar power supply. The electrode loop is connected to a monopolar supply cable to operate in a monopolar mode. The electrode loop is connected to a biopolar power supply cable to operate in a bipolar mode. The manipulator is a thumb loop that is configured to be manipulated by sliding along a first axis to thereby move the surgical tool along the longitudinal axis, the thumb loop being configured to freely rotate about the first axis. A distal-most end of the inner shaft includes a cap portion that protrudes distally beyond a distal-most end of the outer sheath, the first and second openings being defined in the cap portion. The outer sheath, the inner shaft, and the handle portion can be injection molded. in some aspects, the outer sheath and at least a portion of the inner shaft can be made of metal, and the proximal body can be made of plastic. In some aspects, the outer sheath, the inner shaft, and the handle portion can be made from one or more materials that cannot be sterilized at temperatures greater than 120° C. The image sensor is a CMOS sensor that is provided at the distal end of the inner shaft. The light source is a light emitting diode (LED) that is provided at the distal end of the inner shaft. The outer sheath is slidably coupled to the inner shaft. The outer sheath is integrally formed with the inner shaft. The distal end of the inner shaft may include an atraumatic tip. The optical assembly is integrally formed with the inner shaft.

The devices, system, and techniques described herein may provide one or more of the following advantages. For example, a disposable system is provided that incorporates a surgical device with a high frequency shielded digital imaging and illumination system with integrated high frequency instruments. The surgical device provides a hygienic, ergonomic, and economical resectoscope system with disposable components. The system advantageously improves patient safety by preventing improperly cleaned, improperly sterilized, improperly reprocessed, and improperly assembled surgical devices (e.g., resectoscopes) by providing a prepacked, preassembled, and sterilized system. The surgical device can include integrated high frequency instruments, an integrated or removable outer sheath, high frequency capability in both monopolar and bipolar modes, and can be compatible with various high frequency generators. The surgical device can include an integrated imaging system that is disposable with the surgical device and facilitates improved ergonomics of the surgical device over present rod lens designs that are expensive and heavy.

The details of one or more implementations are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

This document generally relates to devices, systems, and methods related to surgical devices. Specifically, a surgical device that can assist in examining and treating patients while utilizing endoscopic-based or laparoscopic-based therapies. For example, surgical devices that facilitate the visualization and treatment of a target area using a disposable resectoscope system that includes a surgical tool and an optical assembly.

Figure 1:
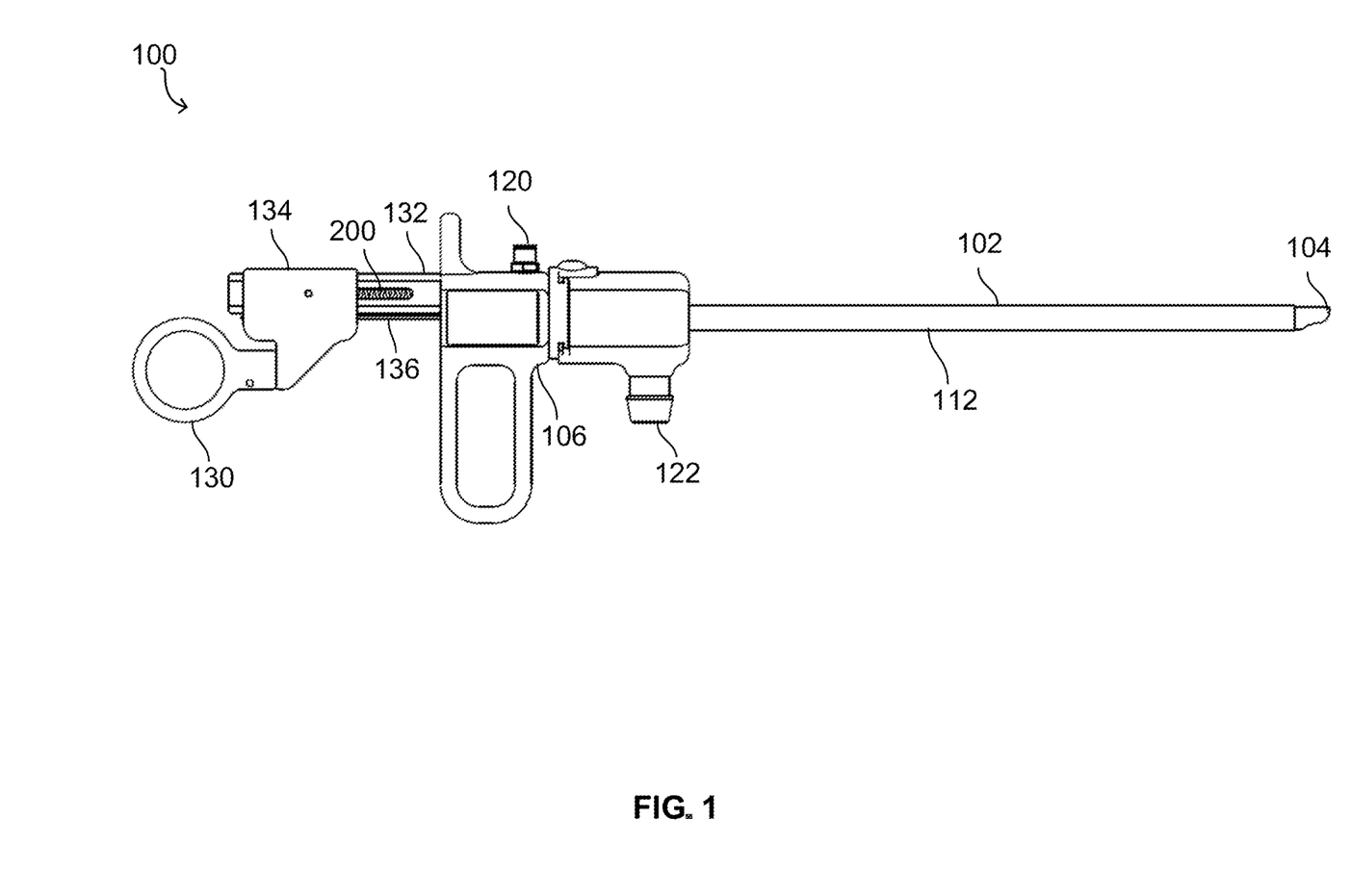
FIG. 1 shows a right-side view of an example surgical device system with a removable external sheath.
Figure 2A:
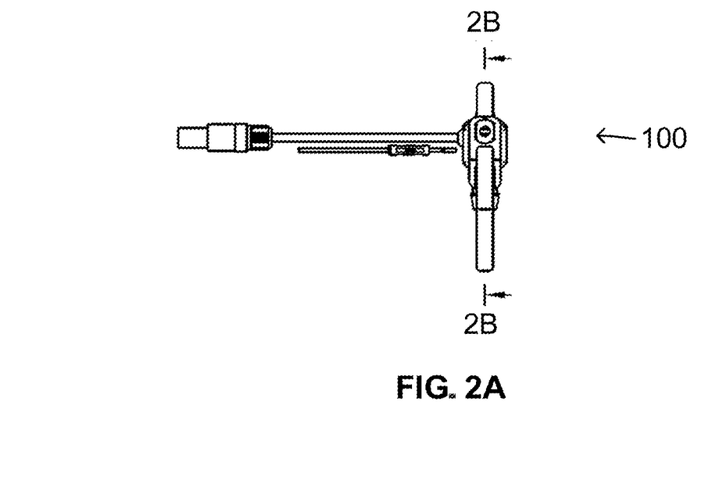
FIG. 2A shows a distal end view of the surgical device of FIG. 1.
Figure 2B:
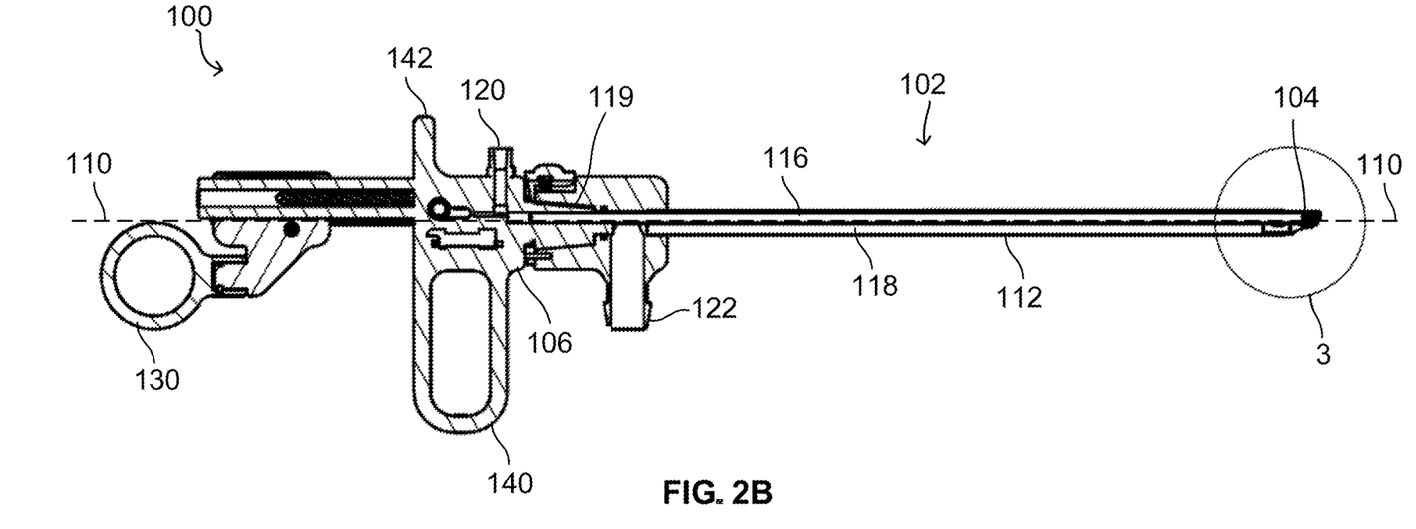
FIG. 2B shows a section view of the surgical device along section 2B-2B of FIG. 2A.

Referring to the figures, FIGS. 1, 2A, and 2B illustrate an example surgical device 100 as described herein. In some aspects, the surgical device 100 can be a resectoscope and/or an endoscope that has a shaft portion 102 that surrounds one or more working channels, an optical assembly at a distal end 104 of the surgical device 100, and a proximal body 106 that has one or more ports and one or more manipulators for controlling the surgical device 100.

The shaft portion 102 extends along a longitudinal axis 110 of the surgical device 100. In some aspects, the shaft portion 102 can be configured to be inserted into a patient's body. The shaft portion 102 can include an outer sheath 112 and an inner shaft 114 that is provided within the outer sheath 112. Each of the outer sheath 112 and the inner shaft 114 can extend distally from the proximal body 106 to the distal end 104 of the surgical device 100.

The outer sheath 112 and inner shaft 114 can each define one or more channels that extend through the shaft portion 102. For example, a first channel 116 and a second channel 118 can extend from the proximal body 106 to the distal end 104. In some aspects, the first channel 116 and the second channel 118 can be formed in either or both of the outer sheath 112 and the inner shaft 114.

The first channel 116 and the second channel 118 of the outer sheath 112 and inner shaft 114 can be configured to provide a connection between the proximal body 106 and the distal end 104 through the shaft portion 102. In some aspects, the connection between the proximal body 106 and the distal end 104 can be configured for fluid communication through the channels in the outer sheath 112 and inner shaft 114. In some aspects, one or more of the channels in the outer sheath 112 and inner shaft 114 can be configured to receive a surgical tool that is moveable along the longitudinal axis 110.

The proximal body 106 can be connected to the shaft portion 102 and positioned proximally to the shaft portion 102. In some aspects, the outer sheath 112 can be detachable from the proximal body 106. For example, the outer sheath 112 can be connected to the proximal body 106 via a tapered connection 119 that facilitates attachment and detachment of the outer sheath 112 to the proximal body 106

The proximal body 106 can include a first port 120 that is in fluid connection with the first channel 116. The first port 120 can be configured to introduce one or more fluids into the first channel 116. In some aspects, the first port 120 includes a luer style connection that facilitates connection between the first port 120 and a fluid source. The first port 120 can extend outwardly from a top surface of the proximal body 106.

The proximal body 106 can also include a second port 122 that is in fluid connection with the second channel 118. The second port 122 can be configured to extract one or more fluids from the second channel 118. The second port 122 can protrude from a bottom surface of the proximal body 106, and can be configured to connect to one or extraction sources that can pull fluid out of the second channel 118 via the second port 122.

A manipulator 130 can be positioned at the proximal end of the proximal body 106. The manipulator 130 can be connected to a sliding connection 132 via a connection member 134. The sliding connection 132 can connect the manipulator 130 to the proximal body 106. The connection member 134 can connect the manipulator 130 to the sliding connection 132, and the connection member 134 can position the manipulator 130 with respect to the sliding connection 132. The compression spring 200 can provide force to retract the connection member 134 along the sliding connection 132 to a proximal position. For example, the manipulator 130 can be positioned below the sliding connection 132 to facilitate longitudinal movement of the manipulator 130 along the sliding connection 132 when a user moves the manipulator 130 longitudinally along the sliding connection 132. In some aspects, the longitudinal movement of the manipulator 130 along the sliding connection 132 that can be aligned with the longitudinal axis 110.

The manipulator 130 can include a loop that provides ergonomic hand positioning and control. For example, the manipulator 130 can control the longitudinal position of a surgical instrument 136 that extends through the surgical device 100 by controlling the extension and retraction of the surgical instrument 136. In some aspects, the manipulator 130 can be rotatably connected to the connection member 134. The rotatable connection between the manipulator 130 and the connection member 134 can facilitate the rotation of the manipulator 130 to provide a user improved ergonomics by allowing the user to adjust the rotational orientation of the manipulator 130 with respect to the connecting member 134.

In some aspects, the proximal body 106 can include a grip 140 and a lever 142. The grip 140 and lever 142 can provide the user improved ergonomics and handling options. The grip 140 can be a looped handle that extends from the bottom surface of the proximal body 106. The lever 142 can be an arm that extends from a top surface of the proximal body 106. The grip 140 and the lever 142 can provide stabilization to the surgical device 100 during use by providing the user additional gripping areas.

The components proximal to the shaft portion 102, including at least the proximal body 106, the manipulator 130, the connection member 134, the sliding connection 132, the grip 140, and the lever 142 can be constructed of various materials, including, but not limited to: metals or plastics, and can be produced by injection molding, machining, and additive manufacturing processes, among others.

Figure 3:
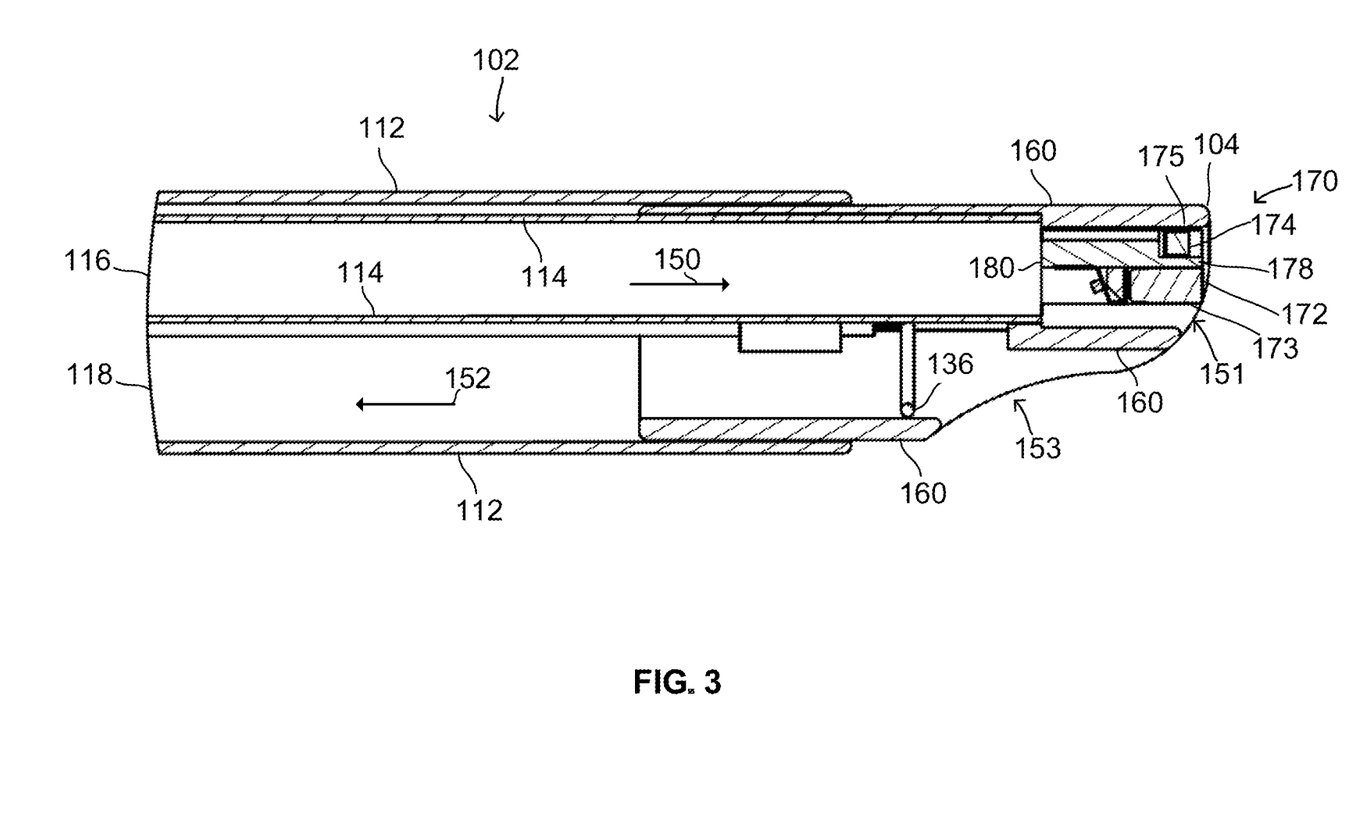
FIG. 3 shows a detailed section view of a distal portion 3 of FIG. 2B.

Referring to FIG. 3, a detailed section view of the area 3 of FIG. 2B is illustrated. The outer sheath 112 can surround the inner shaft 114, and each of the outer sheath 112 and inner shaft 114 can define the first channel 116 and the second channel 118. For example, the first channel 116 can be formed within the inner shaft 114 and the second channel 118 can be formed between the outer sheath 112 and the inner shaft 114.

The first channel 116 can provide a first flow path 150 through the first channel 116 between the proximal end of the shaft portion 102 and a first opening 151 provided at a distal end 104 of the shaft portion 102. The first flow path 150 can extend from the first port 120 to the first opening 151 through the first channel 116.

The second channel 118 can provide a second flow path 152 between the proximal end of the shaft portion 102 and a second opening 153 provided at the distal end 104 of the shaft portion 102. The second flow path 152 can extend from the second opening 153 to the second port 122 through the second channel 118. In some aspects, the second flow path 152 is distinct from the first flow path 150.

Figure 4:
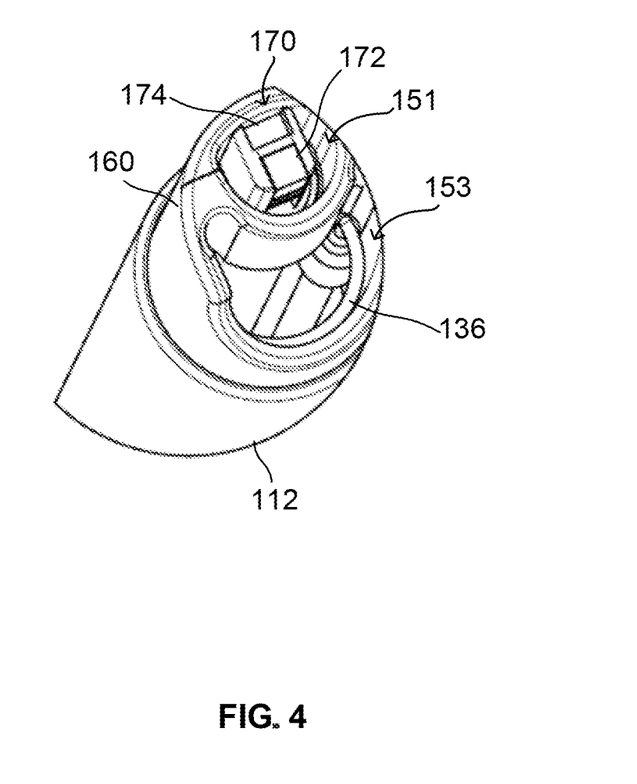
FIG. 4 shows a perspective view of a distal portion of the surgical device of FIG. 1

In some aspects, the distal end 104 includes a cap 160 that protrudes distally beyond a distal-most end of the outer sheath 112. The cap 160 can extend from the distal end of the inner shaft 114, and can extend distally beyond a distal most end of each of the outer sheath 112 and the inner shaft 114. In some aspects, the distal most end of the inner shaft 114 is distal of the distal most end of the outer sheath 112. The first opening 151 and the second opening 153 can be formed in the cap 160. As illustrated in FIGS. 3 and 4, the surgical device 100 can include an optical assembly 170 that is provided at the distal end 104 of the inner shaft 114. The optical assembly 170 can protrude radially inward from an interior surface of the first channel 116. The optical assembly 170 includes a light source 174 and an imaging sensor 172. In some aspects, the cap 160 includes a light source recess 175 and an imaging sensor recess 173 that are dimensioned to receive each of the light source 174 and the imaging sensor 172, respectively. In some aspects, the light source 174 and the imaging sensor 172 are integral with the surgical device 100. For example, the light source 174 and the imaging sensor 172 can be integrated into the cap 160, the inner shaft 114, and the outer shaft 112.

In some aspects, the light source 174 is provided to illuminate a target area in a patient for imaging by the imaging sensor 172. The light source 174 can be a light emitting diode (LED) that is provided at the distal end 104 of the inner shaft 114. In some aspects, the light source 174 can be a proximal LED that includes a fiberoptic connection from the proximal body 106 to the light source 174.

The imaging sensor 172 can be positioned at the distal end 104 of the surgical device 100 to provide imaging and guidance of the surgical device 100 in the target area of the patient to the medical operator. In some aspects, the imaging sensor 172 can be a camera, a complementary metal oxide semiconductor (CMOS) imager, active pixel sensor (APS), a charged coupled device (CCD). The distal imaging sensor can be wired to a proximal electronics located in 106 and may then communicate, either by wire or wirelessly, images, videos, and other sensed data to a medical operator. The imaging sensor 172 can include electrical shielding that rejects high frequency interference that can be present at the target area (e.g., via high-frequency surgical tools).

In some aspects, the first opening 151 is formed between the optical assembly 170 and the inner shaft 114 to at least partially surround the optical assembly 170. The first opening 151 is configured to direct fluid from the first channel 116 across a distal surface 178 of the optical assembly 170. The directed fluid through the first opening 151 across a distal surface 178 of the optical assembly can facilitate a rinsing of the optical assembly 170 to provide a clearer imaging result to the medical operator. The directed fluid can be a fluid that is chosen for rinsing the optical assembly 170, or can be a fluid that is used for treatment in the target area, and rinses the optical assembly 170 as well. In some cases, the first opening 151 and/or the optical assembly 170 can be shaped to create and direct turbulent flow around the light source 174 and/or the imaging sensor 172 to further provide a cleaning effect.

In some aspects, a cross-sectional area of the first channel 116 is greater than a cross-sectional area of the first opening 151. The first channel 116 can be configured to impinge fluid traveling along the first flow path 150 against a proximal surface 180 of the optical assembly 170. The proximal surface 180 of the optical assembly 170 can direct fluid to the first opening 151. The first opening 151 is configured to inject fluid to the target area (e.g., a surgical site). The second opening 153 is configured to suction fluid from the target area (e.g., the surgical site) into the second channel 118.

The surgical instrument 136 can extend through the second channel 118, and can be positioned in or near the second opening 153. The second opening 153 can extend partially around the optical assembly 170 and the first opening 151. In some aspects, the surgical instrument 136 and the second opening 153 can each have curved profile such that the curved profile of a distal end of the surgical instrument is compatible to extend through the curved profile of the second opening 153.

In some aspects, the outer sheath 112, the inner shaft 114, the proximal body 106, and the manipulator 130 can be injection molded. The outer sheath 112, the inner shaft 114, the proximal body 106, and the manipulator 130 can be made from one or more materials that cannot be sterilized at high temperatures, for example at temperatures greater than around 120° C. that may be used in steam autoclaves. Such materials can include plastics that may flow, wrap, or otherwise deform at temperatures greater than 120° C. In some such cases, materials that begin to deform at temperatures greater than 140° C. may be used. In some cases, one or more of the above-mentioned parts can be made by 3D printing or other types of additive manufacturing techniques.

Figure 5:
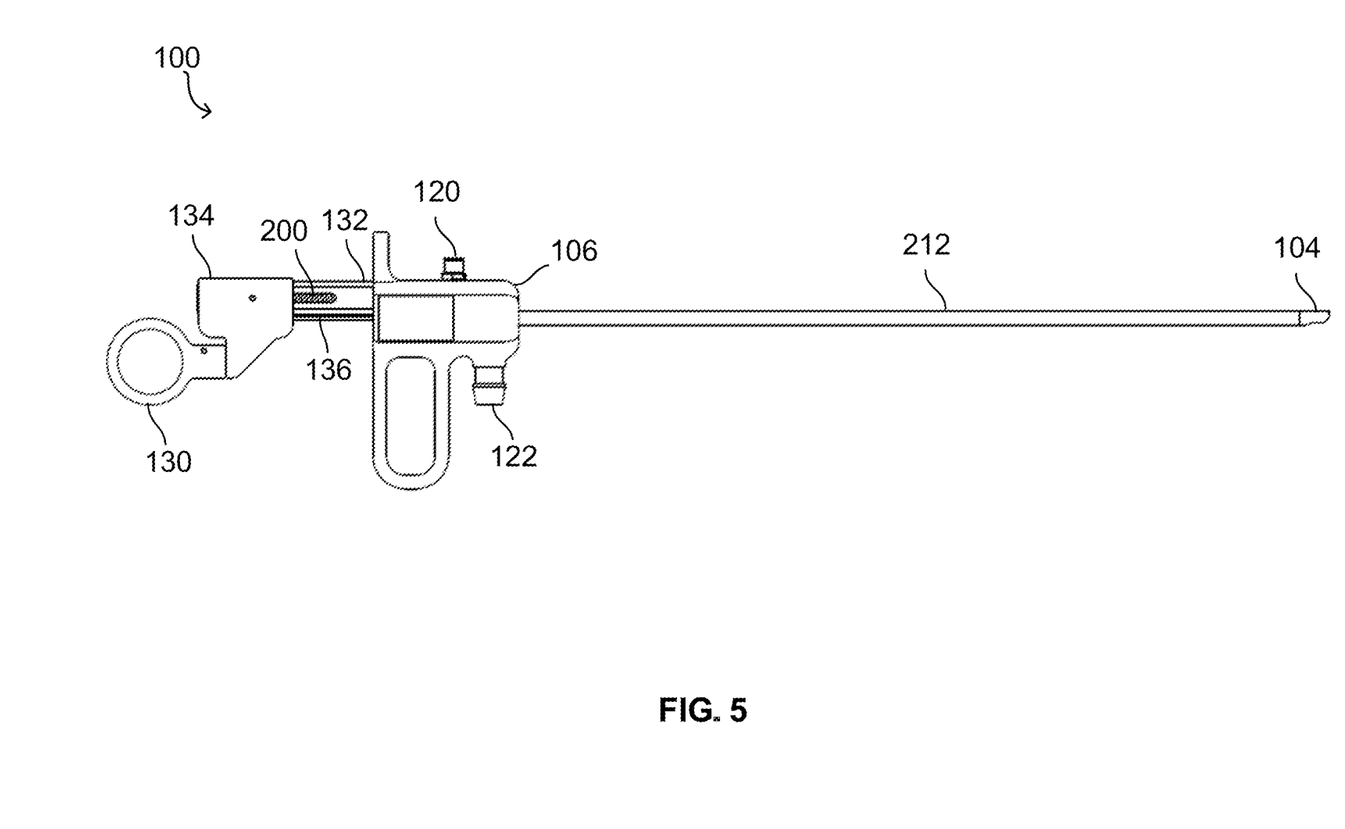
FIG. 5 shows a right-side view of an example surgical device system with an integral external sheath
Figure 8:
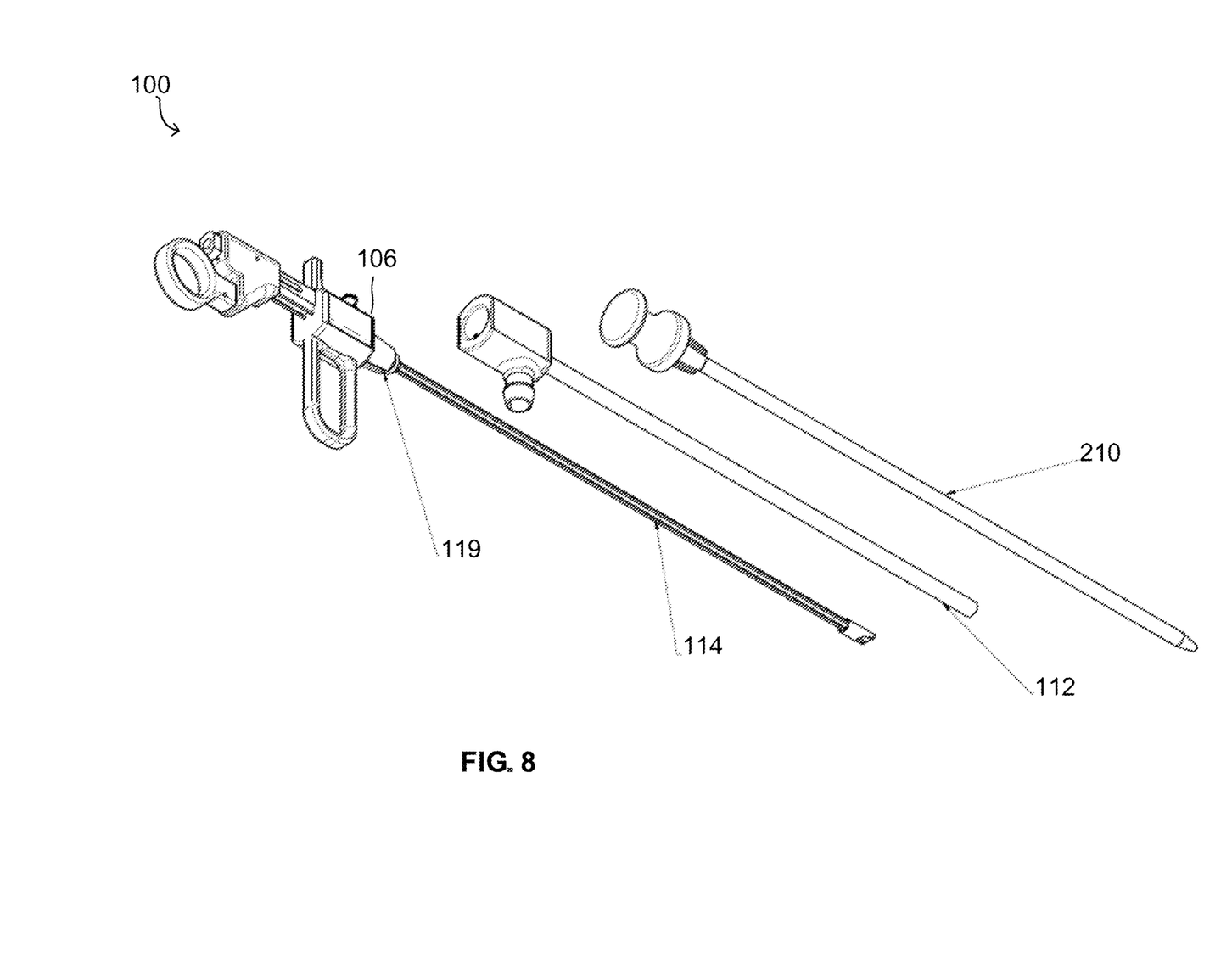
FIG. 8 shows a perspective view of a surgical device of FIG. 1 with a detachable external insertion sheath and insertable obturator

FIG. 5 illustrates the surgical device 100 that has an integral outer sheath 212. The surgical device 100 of FIG. 5 can share features with the surgical device 100 of FIGS. 1-4. The integral outer sheath 212 can be integral with the surgical device 100 such that the integral outer sheath 212 may not be removed from the surgical device 100. In other aspects, the outer sheath 112 can be removed from the surgical device 100, as shown in FIG. 8.

Figure 6A:
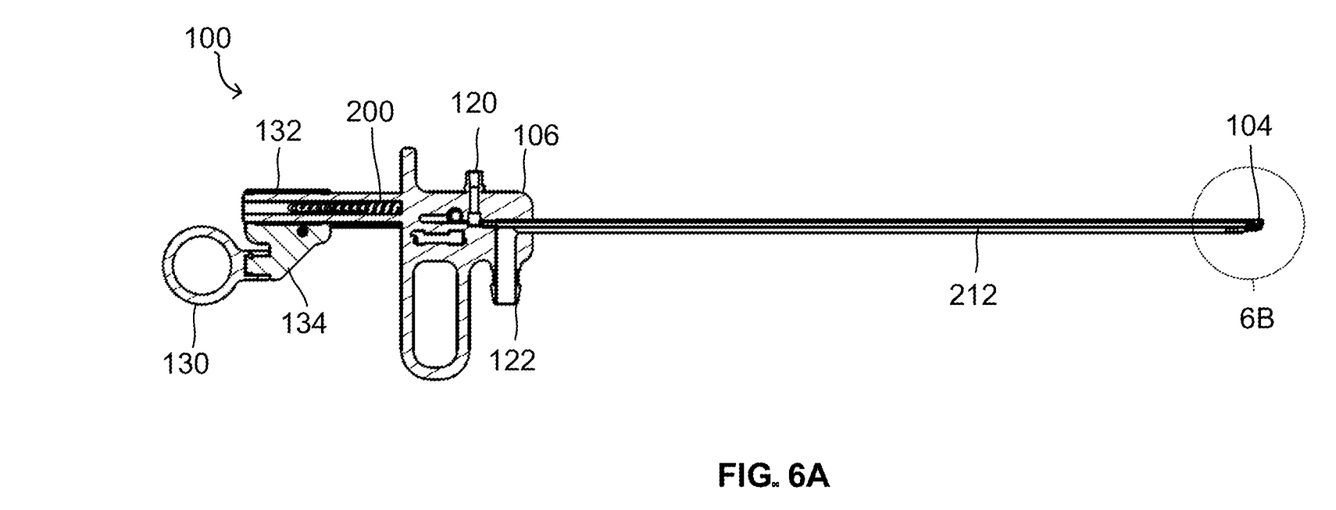
FIG. 6A shows a section view of the surgical device of FIG. 5.
Figure 6B:
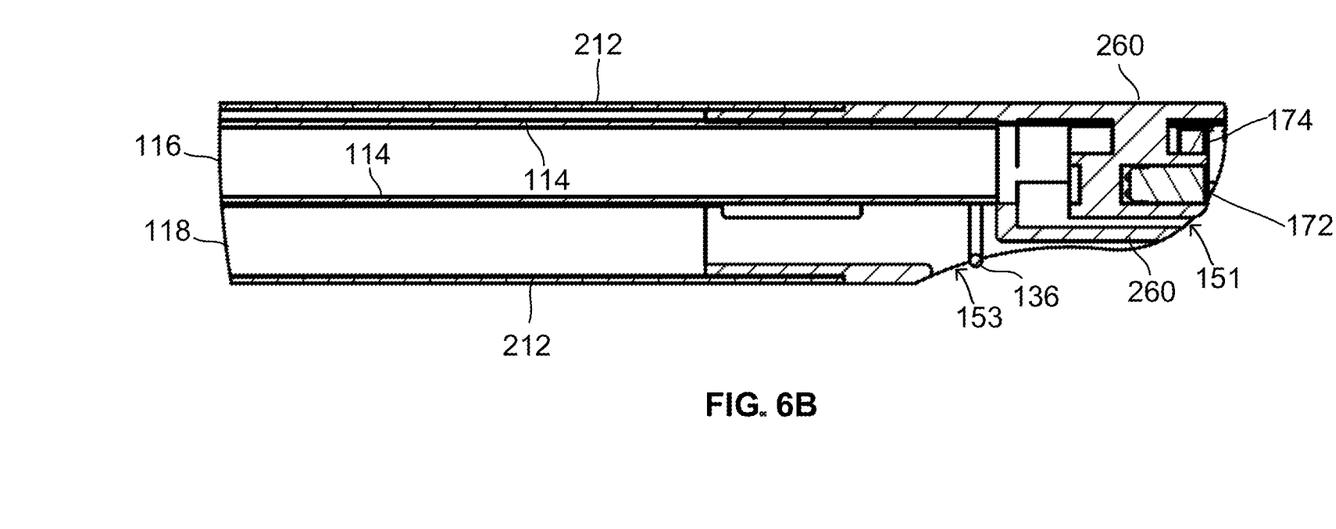
FIG. 6B shows a detailed section view of a distal portion 6B of FIG. 6A.

Referring to FIGS. 6A and 6B, the surgical device 100 is shown with an integral outer sheath 212. In some aspects, the distal end 104 includes a cap 260 that is attached to both the inner shaft 114 and the integral outer sheath 212. The cap 260 can extend from the distal end of the inner shaft 114, and can extend distally beyond a distal most end of each of the outer sheath 212 and the inner shaft 114.

Figures 7A, 7B:
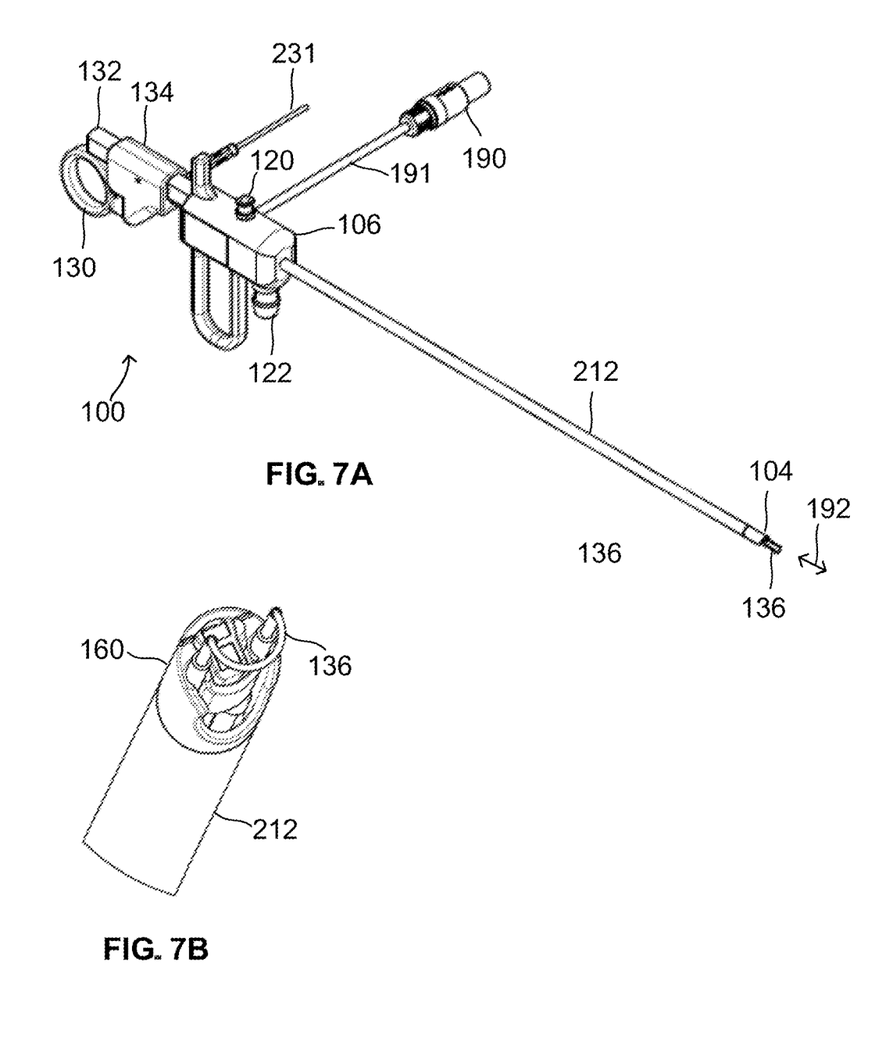
FIG. 7A shows a perspective view of the surgical device of FIG. 5 with a surgical instrument in an extended position.
FIG. 7B shows a perspective view of a distal end of the surgical device of FIG. 7A.
Figure 7C:
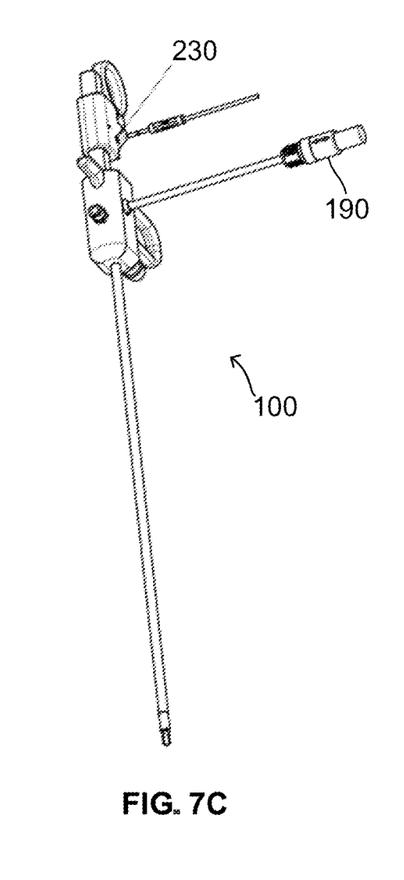
FIG. 7C shows a rear perspective view of the surgical device of FIG. 7A.

Referring to FIGS. 7A, 7B, and 7C, the surgical device 100 is shown in an extended position, where the surgical instrument 136 is extended outside of the distal end 104 of the surgical device 100. In some aspects, the proximal body 106 includes an electrical connection 190 that can provide power to the optical assembly 170 and can transmit imaging signals including images and video from the optical assembly 170. In some aspects, the proximal body 106 also includes an electrical connection 230 that can provide current to the surgical instrument 136, including high-frequency current to the surgical instrument 136. The electrical connections 190 and 230 can include an umbilical 191 and 231 that can be integral with the proximal body 106 or can be removable from the proximal body 106.

The surgical instrument 136 can be extended by the medical operator. The medical operator can actuate the manipulator 130 distally, causing the connection member 134 to slide distally over sliding connection 132. The extended position of the surgical instrument 136 includes axial motion 192 that can be along the longitudinal axis 110.

The surgical instrument 136 can be retracted into the surgical device 100 (as shown in FIGS. 1-6). The retracted position of the surgical instrument 136 provides a safe and isolated location for the surgical instrument 136 when the surgical instrument 136 is not in use. The surgical instrument 136 can be automatically retracted when the manipulator 130 is released by the medical operator. The automatic retraction of the surgical instrument 136 can be facilitated by a compression spring 200 that is positioned within the sliding connection 132. The compression spring 200 compresses when the manipulator 130 is slid into the extended position, and the compression spring 200 releases when the operator force at the manipulator 130 is released. The release of the compression spring 200 returns the surgical device 100 to the retracted position where the surgical instrument 136 is retracted into outer sheath 112.

In some aspects, the axial motion 192 of the surgical instrument 136 may have various linear travel limits to provide optimal extension of the surgical instrument 136 from the distal end 104 of the surgical device 100. The distal end 104 of the shaft portion 102 can be designed to be atraumatic to prevent patient injury and can be composed of electrically isolative materials.

FIG. 8 shows that the surgical device 100 can be configured such that the outer sheath 112 is detachable from the inner shaft 114 and other components that are contained within the outer sheath 112. The outer sheath 112 can be detachable via the tapered connection 119 to the proximal body 106, the tapered connection 119 provides fixation and orientation of the outer sheath 112. This feature providing two key functions:

The outer sheath 112 that is detached can be fitted with an internal obturator 210 and inserted into the body prior to the insertion the inner shaft 114. The obturator 210 and outer sheath 112 can provide atraumatic access and expansion of the bodily orifice. After insertion, the obturator 210 can be removed and replaced by the inner shaft 114. The inner shaft 114 may be removed from the outer sheath 112 at any time during the procedure thus providing a large working channel for fast extraction of fluids or biologics from the body and/or for the extraction of large material(s) to pass out of the body that otherwise would not be able to be received in a smaller channel.

The shaft portion 102 and the detachable outer sheath 112 can be constructed of various metals including shape memory alloys (e.g., Nitinol) or high strength plastics to provide optimal flexibility characteristics. The outer sheath 112 can be of various diameters.

Figures 9A, 9B:
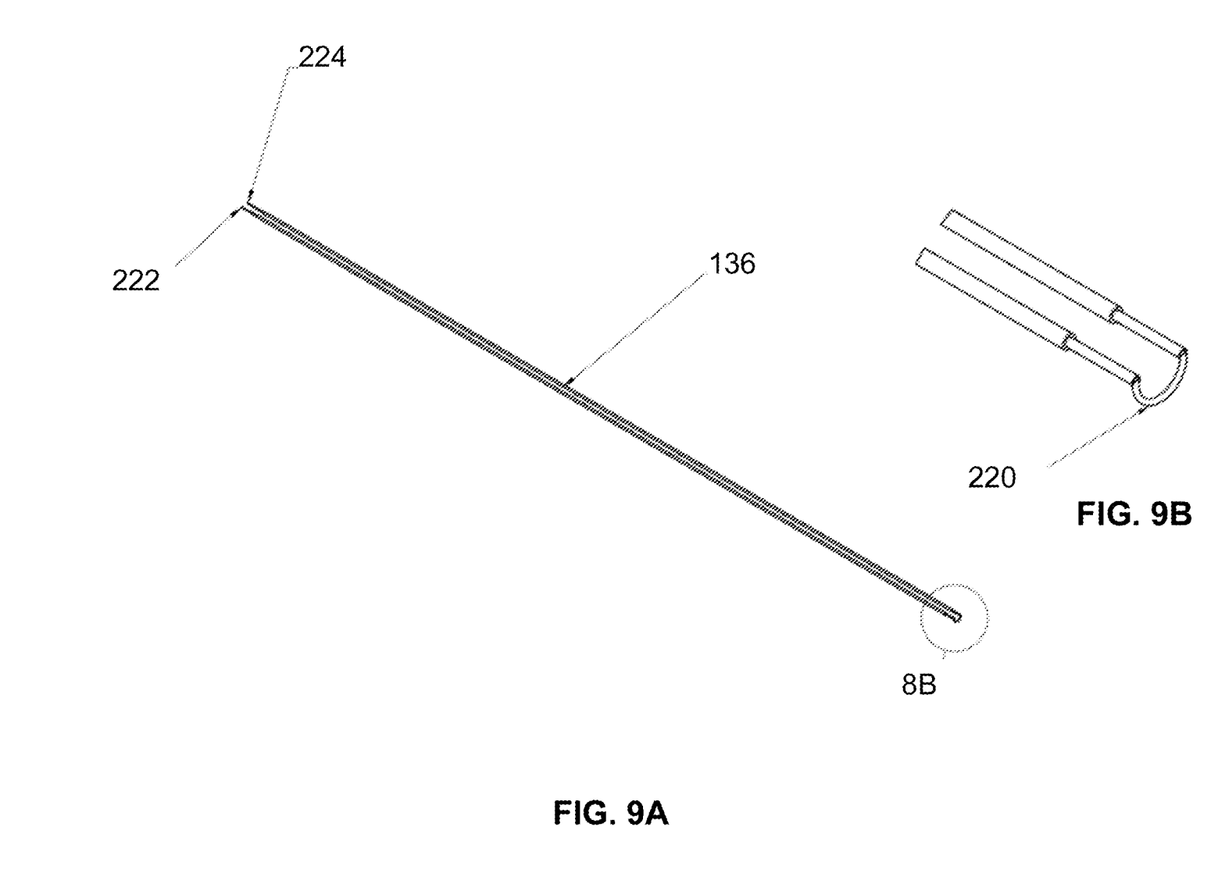
FIG. 9A shows a perspective view of an example high frequency instrument.
FIG. 9B shows a detail view of the distal end of FIG. 9A.

FIGS. 9A and 9B show the exemplary surgical instrument 136 removed from the surgical device 100. In some aspects, the surgical instrument 136 can be a resecting loop that operates as a tissue resecting device via the application of high frequency current to a distal wire 220. The surgical tool 136 can be connected to a high-frequency power supply, and the power supply can apply HF current to the proximal connections 222, 224. The current applied to the proximal connections 222, 224 can travel along the length of the surgical instrument 136 and be delivered to the distal wire 220, the distal wire 220 can be configured to cut, remove, coagulate, or ablate tissue. The distal wire 220 can be of various shapes and configurations to optimally cut, coagulate, or ablate tissue.

Figure 10:
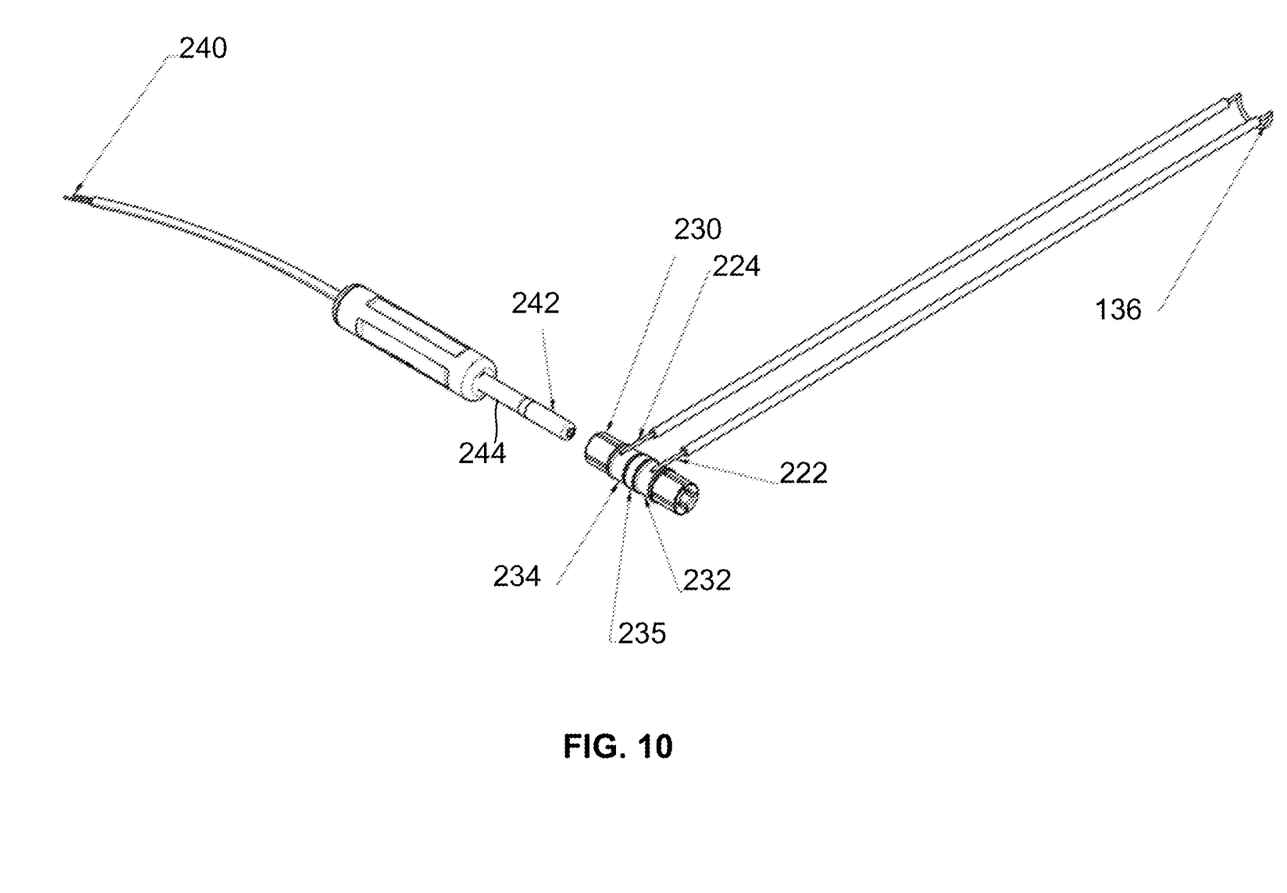
FIG. 10 shows a perspective view of a high frequency instrument with a bipolar connection.

FIG. 10 shows a first example of a grounding path for the current supplied to the surgical instrument 136. The grounding path of the current may be via the proximal connections 222, 224 exiting at a connection 230 on the proximal body 106. The grounding path of FIG. 10 is a bipolar grounding path that includes a positive connection 232 that connects to the proximal connection 222 and a negative connection 234 that connects to the proximal connection 224. An electrical insulator 235 can be positioned between the positive connection 232 and the negative connection 234. The connection 230 can interface with a power supply connection that includes a positive connection 242 and a negative connection 244 that connect to the bipolar power supply via connection line 240.

Figure 11:
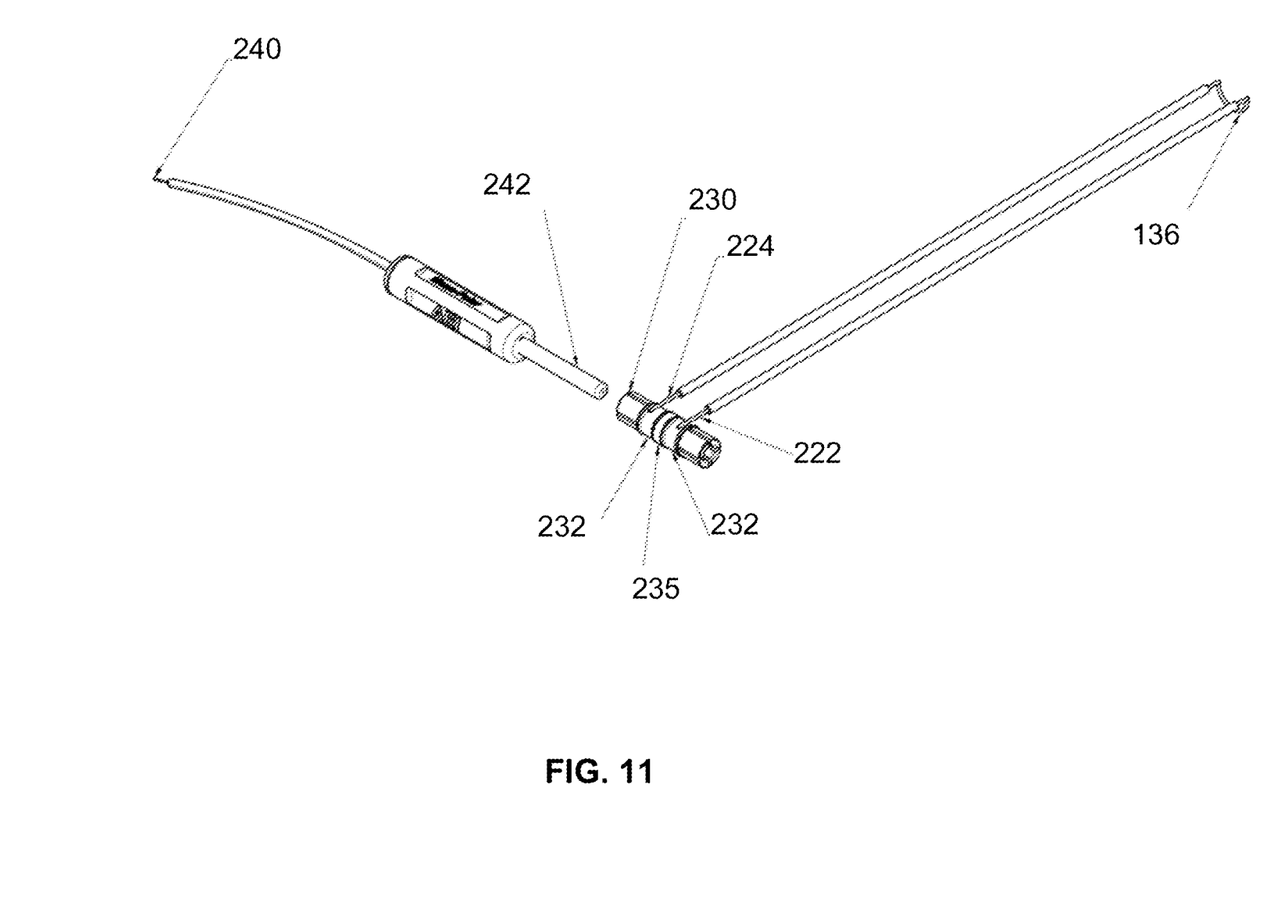
FIG. 11 shows a perspective view of a high frequency instrument with a monopolar connection.

FIG. 11 shows a second example of a grounding path for the current supplied to the surgical instrument 136. The grounding path of the current may be via the proximal connections 222, 224 exiting through the patient body via conductive fluids and/or tissues. The patient is externally grounded. The grounding path of FIG. 11 is a monopolar grounding path that includes two positive connections 232 that connect to the proximal connections 222, 224. An electrical insulator 235 can be positioned between the positive connections 232. The connection 230 can interface with a power supply connection that includes a positive connection 242 that connects to the monopolar power supply via connection line 240.

The surgical instrument 136 and the proximal connectors 222, 224 are proximally attached to the connection member 134 of the proximal body 106. In some aspects, the surgical device 100 can be configured to be both a monopolar design and a biopolar design. For example, the surgical device 100 can be configured to be connected to a monopolar power supply and to a bipolar power supply. In some aspects, the proximal connectors (e.g., proximal connectors 222, 224, 242, 244) can connect to the supply line 240. The supply line 240 can provide either a monopolar connection or a bipolar connection. In either case, the proximal connectors can facilitate a connection to each power supply type without changes to the surgical device 100. The surgical instrument 136 can be integrated into the surgical device 100.

In operation, the surgical device 100 can be removed from sterile packaging, attached to ancillary power and control devices (e.g., Video control, HF control, and fluid control), and checked for function. The surgical device 100 can be fully disposable for hygienic reasons and ease of sterilization. The surgical device 100 can be compact, providing optimized disposal.

The surgical device 100 can allow extension and retraction of the surgical instrument 136, and the surgical instrument 136 can facilitate the cutting and ablating of tissues in the target area, and the surgical device 100 includes the first opening 151 and the second opening 153 for infusion and extraction of fluids and biologics to and from the body. The surgical device 100 may allow bi-directional passage of both fluids and biological matter (i.e., continuous flow). The optical assembly 170 can provide a clear view of the procedure. The surgical device 100 can be of various lengths to accommodate different anatomies.

The surgical device 100 can be made to be disposable in the following versions. In one example, the surgical device 100 can include an integral outer sheath 112 that provides a slim outside diameter useful for certain anatomies and applications. In another example, the surgical device 100 can include the outer sheath 112 that is detachable, that provides the medical operator the ability for both intubating the patient and extracting large volumes of materials when the inner shaft 114 is detached from the outer sheath 112.

The surgical device 100 can provide several advantages. For example, the surgical device 100 can be provided as a disposable system that incorporates a resectoscope with a high frequency shielded digital imaging and illumination system and integrated high frequency surgical instruments. The surgical device 100 provides a hygienic, ergonomic, and economical system with disposable components. The surgical device 100 can advantageously improve patient safety by preventing improperly cleaned, improperly sterilized, improperly reprocessed, and improperly assembled resectoscopes by providing a prepacked, preassembled, and sterilized system. The surgical device 100 can include integrated high frequency surgical instrument(s) 136, an integrated or removable outer sheath 112, high frequency capability in both monopolar and bipolar modes, and can be compatible with various high frequency generators. The surgical device 100 can include an integrated optical assembly 170 that is disposable with the surgical device 100 and facilitates improved ergonomics of the resectoscope over present rod lens designs that are expensive and heavy.

While this specification contains many specific implementation details, these should not be construed as limitations on the scope of the disclosed technology or of what may be claimed, but rather as descriptions of features that may be specific to particular implementations of particular disclosed technologies. Certain features that are described in this specification in the context of separate implementations can also be implemented in combination in a single implementation in part or in whole. Conversely, various features that are described in the context of a single implementation can also be implemented in multiple implementations separately or in any suitable sub combination. Moreover, although features may be described herein as acting in certain combinations and/or initially claimed as such, one or more features from a claimed combination can in some cases be excised from the combination, and the claimed combination may be directed to a sub combination or variation of a sub combination. Similarly, while operations may be described in a particular order, this should not be understood as requiring that such operations be performed in the particular order or in sequential order, or that all operations be performed, to achieve desirable results. Particular implementations of the subject matter have been described. Other implementations are within the scope of the following claims.

What is claimed is:

1. A device comprising:
a shaft portion that extends along a longitudinal axis, the shaft portion comprising:
an outer sheath,
an inner shaft provided within the outer sheath,
an optical assembly provided at a distal end of the inner shaft, the optical assembly including a light source and an imaging sensor; and
a handle portion that is coupled to a proximal end of the shaft portion,
wherein a first channel that extends along the longitudinal axis is defined by one or both of the outer sheath and the inner shaft, the first channel providing a first flow path between the proximal end of the shaft portion and a first opening provided at a distal end of the shaft portion, the first opening being provided between the optical assembly and the inner shaft to partially surround the optical assembly on three sides,
wherein a second channel that extends along the longitudinal axis is defined by one or both of the outer sheath and the inner shaft, the second channel providing a second flow path between the proximal end of the shaft portion and a second opening provided at the distal end of the shaft portion, the second flow path being distinct from the first flow path,
wherein the optical assembly is provided at a distal end of the first channel to thereby partially block and divert the first flow path around the optical assembly to the first opening, the first opening and the optical assembly being configured to direct turbulent fluid flow (i)

around the light source and the imaging sensor and (ii) across a distal surface of the optical assembly, wherein a surgical tool is provided in the second channel; and wherein the first channel is configured to direct fluid into contact with a proximal surface of the optical assembly, the proximal surface facing the proximal end of the shaft portion.

2. The device of claim 1, wherein the optical assembly protrudes radially inward from an interior surface of the first channel.

3. The device of claim 1, wherein the turbulent fluid flow through the first opening across the distal surface of the optical assembly facilitates a rinsing of the distal surface of the optical assembly.

4. The device of claim 1, wherein a cross-sectional area of the first channel is greater than a cross-sectional area of the first opening.

5. The device of claim 1, wherein the first opening is configured to inject fluid to a surgical site, and wherein the second opening is configured to remove fluid and biologics from the surgical site.

6. The device of claim 5, wherein the handle portion includes:
- a first port that is in fluid connection with the first channel and that is configured to introduce fluid into the first channel, and
- a second port that is in fluid connection with the second channel and that is configured to extract fluid and biologics from the second channel.

7. The device of claim 1, wherein the surgical tool is configured to be movable along the longitudinal axis.

8. The device of claim 7, wherein the surgical tool is a high-frequency (HF) electrode that is configured to be connected to an HF power supply.

9. The device of claim 8, wherein the high-frequency electrode is configured to operate in a monopolar mode based on being connected to a monopolar power supply and configured to operate in a bipolar mode based on being connected to a bipolar power supply.

10. The device of claim 9, wherein the high-frequency electrode is connected to a monopolar supply cable to operate in a monopolar mode.

11. The device of claim 9, wherein the high frequency electrode is connected to a bipolar power supply cable to operate in a bipolar mode.

12. The device of claim 1, wherein the handle portion includes a thumb loop that is configured to be manipulated by sliding along a first axis to thereby move the surgical tool along the longitudinal axis, the thumb loop being configured to freely rotate about the first axis.

13. The device of claim 1, wherein the outer sheath, the inner shaft, and the handle portion are made from one or more materials that cannot be sterilized at temperatures greater than 120° C.

14. The device of claim 1, wherein the imaging sensor is a CMOS sensor that is provided at the distal end of the inner shaft.

15. The device of claim 1, wherein the light source is a light emitting diode (LED) that is provided at the distal end of the inner shaft.

16. The device of claim 1, wherein the outer sheath is slidably coupled to the inner shaft.

17. The device of claim 1, wherein the outer sheath is integrally formed with the inner shaft.

18. The device of claim 1, wherein the distal end of the shaft portion comprises electrically isolative materials.

19. The device of claim 1, wherein the optical assembly is integrally formed with the inner shaft.

* * * * *